(12) United States Patent
Flanagan

(10) Patent No.: US 10,583,006 B2
(45) Date of Patent: Mar. 10, 2020

(54) TRANSCATHETER AORTIC VALVULOPLASTY DEVICE

(71) Applicant: BOSTON SCIENTIFIC SCIMED, INC., Maple Grove, MN (US)

(72) Inventor: Aiden Flanagan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 405 days.

(21) Appl. No.: 15/416,704

(22) Filed: Jan. 26, 2017

(65) Prior Publication Data

US 2017/0143487 A1    May 25, 2017

Related U.S. Application Data

(63) Continuation of application No. 13/909,575, filed on Jun. 4, 2013, now abandoned.

(60) Provisional application No. 61/661,599, filed on Jun. 19, 2012.

(51) Int. Cl.
| | |
|---|---|
| *A61F 2/24* | (2006.01) |
| *A61M 25/10* | (2013.01) |
| *A61B 17/22* | (2006.01) |
| *A61B 17/00* | (2006.01) |

(52) U.S. Cl.
CPC ............ *A61F 2/2436* (2013.01); *A61B 17/22* (2013.01); *A61F 2/2418* (2013.01); *A61F 2/2427* (2013.01); *A61M 25/1002* (2013.01); *A61M 25/104* (2013.01); *A61B 2017/00783* (2013.01); *A61B 2017/22061* (2013.01); *A61B 2017/22098* (2013.01); *A61F 2/243* (2013.01); *A61F 2210/0014* (2013.01); *A61M 25/1018* (2013.01); *A61M 2025/1004* (2013.01)

(58) Field of Classification Search
CPC .......... A61F 2/2418; A61F 2220/0016; A61M 25/104; A61M 2025/1004; A61B 2017/00783; A61B 2017/22061; A61B 2017/22098

See application file for complete search history.

(56) References Cited

U.S. PATENT DOCUMENTS

| | | |
|---|---|---|
| 5,257,974 A | 11/1993 | Cox |
| 7,329,279 B2 | 2/2008 | Haug et al. |
| 7,381,219 B2 | 6/2008 | Salahieh et al. |
| 7,445,631 B2 | 11/2008 | Haug et al. |
| 7,748,389 B2 | 7/2010 | Salahieh et al. |
| 7,780,725 B2 | 8/2010 | Haug et al. |
| 7,824,442 B2 | 11/2010 | Salahieh et al. |
| 7,824,443 B2 | 11/2010 | Salahieh et al. |
| 2003/0028210 A1 | 2/2003 | Boyle et al. |

(Continued)

FOREIGN PATENT DOCUMENTS

| | | |
|---|---|---|
| WO | 2005062980 A2 | 7/2005 |
| WO | 2005065585 A1 | 7/2005 |

(Continued)

*Primary Examiner* — Katherine M Shi

(74) *Attorney, Agent, or Firm* — Seager, Tufte & Wickhem LLP

(57) ABSTRACT

A valvuloplasty device comprises an expandable anchor and an expansion member mounted about an outer surface of the expandable anchor. The expansion member is either an annular balloon or a sleeve. The valvuloplasty device can be used for valvuloplasty and for valve implantation.

19 Claims, 5 Drawing Sheets

(56) References Cited

U.S. PATENT DOCUMENTS

| | | |
|---|---|---|
| 2005/0112355 A1 | 5/2005 | Wycech |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2006/0020327 A1* | 1/2006 | Lashinski ............ A61F 2/2436 623/1.25 |
| 2006/0058872 A1 | 3/2006 | Salahieh et al. |
| 2006/0173524 A1 | 8/2006 | Salahieh et al. |
| 2006/0253191 A1 | 11/2006 | Salahieh et al. |
| 2007/0010876 A1 | 1/2007 | Salahieh et al. |
| 2007/0024452 A1 | 2/2007 | Fitzgerald |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0203503 A1 | 8/2007 | Salahieh et al. |
| 2008/0125859 A1 | 5/2008 | Salahieh et al. |
| 2008/0234814 A1 | 9/2008 | Salahieh et al. |
| 2009/0054969 A1 | 2/2009 | Salahieh et al. |
| 2009/0076598 A1 | 3/2009 | Salahieh et al. |
| 2009/0264997 A1 | 10/2009 | Salahieh et al. |
| 2010/0121434 A1 | 5/2010 | Paul et al. |
| 2010/0280495 A1 | 11/2010 | Paul et al. |
| 2011/0015728 A1* | 1/2011 | Jimenez ............... A61F 2/2418 623/2.11 |
| 2011/0118634 A1 | 5/2011 | Golan |
| 2011/0264039 A1 | 10/2011 | Thielen et al. |
| 2012/0109179 A1 | 5/2012 | Murphy et al. |

FOREIGN PATENT DOCUMENTS

| | | |
|---|---|---|
| WO | 2006009690 A1 | 1/2006 |
| WO | 2007053243 A2 | 5/2007 |
| WO | 2007058847 A2 | 5/2007 |
| WO | 2011083460 A2 | 7/2011 |

\* cited by examiner

TRANSCATHETER AORTIC VALVULOPLASTY DEVICE

CROSS REFERENCE TO RELATED APPLICATIONS

This application is a continuation of U.S. application Ser. No. 13/909,575, filed Jun. 4, 2013, which claims priority to U.S. Patent Provisional Application No. 61/661,599, filed Jun. 19, 2012, the entire contents of which are hereby incorporated herein by reference.

BACKGROUND OF THE INVENTION

Failing heart valves can become calcified and stenotic. Valvuloplasty is a procedure that can break calcification and open up heart valves. With the advent of percutaneous transcatheter heart valve replacement, the importance of valvuloplasty devices and procedures may increase, since a valvuloplasty procedure may be required to facilitate the proper placement and/or expansion of a percutaneously delivered valve. Typically the stenosed aortic valve would need to be opened using a procedure such as a balloon aortic valvuloplasty, prior to insertion of a catheter device and deployment of the replacement heart valve. A balloon opens the valve leaflets wider by a crushing action and cracks calcium deposits, making the leaflets more flexible.

During balloon aortic valvuloplasty, the aortic valve is blocked and a large pressure is created by the left ventricle during systole, and there are several drawbacks to prior art balloon-based valvuloplasty devices as a result of the pressure gradient between the aorta and the ventricle. Rapid pacing of the heart in order to lower the pressure gradient, but such rapid pacing of the heart has risks for the patient. Another problem associated with prior art balloon-based valvuloplasty devices is the tendency of the valvuloplasty balloon to slip out of the stenotic area during the valvuloplasty procedure. Such slippage may, for example, arise as a result of the pressures exerted on the device by blood ejected from the beating heart, or as a function of how the valvuloplasty device inflates.

In view of the drawbacks associated with previously known methods and apparatus for performing valvuloplasty, it would be desirable to provide a device that expands the valve area to remove the stenosis without creating a significant pressure gradient and without requiring pacing of the heart.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. .sctn.1.56 (a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

The valvuloplasty devices described herein are deployed to treat bodily lumens affected by stenosis. In one application, the valvuloplasty devices described herein are used to treat a stenosis in the area of a heart valve. The valvuloplasty devices include an expandable anchor and an expansion member. Methods of using the valvuloplasty devices for valvuloplasty and replacement valve implantation are described herein.

These and other embodiments which characterize the invention are pointed out with particularity in the claims annexed hereto and forming a part hereof. However, for further understanding of the invention reference can be made to the drawings which form a further part hereof and the accompanying descriptive matter, in which there is illustrated and described embodiments of the invention.

BRIEF DESCRIPTION OF THE SEVERAL VIEWS OF THE DRAWING(S)

DETAILED DESCRIPTION OF THE INVENTION

Figure 1:
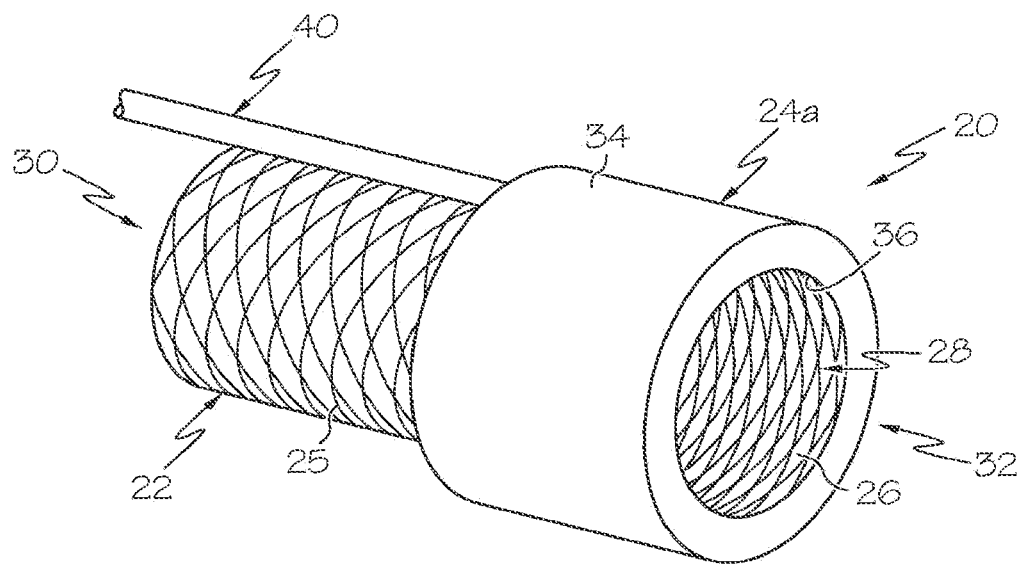
FIG. 1 is a perspective view of a valvuloplasty device in a deployed configuration.

While a valvuloplasty device as described herein may be embodied in many different forms, there are described in detail herein specific preferred embodiments of the valvuloplasty device. This description is an exemplification of the principles of the valvuloplasty device, and use thereof, and is not intended to limit the valvuloplasty device to the particular embodiments illustrated.

For the purposes of this disclosure, like reference numerals in the figures shall refer to like features unless otherwise indicated.

FIGS. 1-6B show a valvuloplasty device 20 that comprises an anchor 22, an expansion member 24, and has a longitudinal axis. As can be seen from the figures, the anchor has a proximal end 30, a distal end 32, and a longitudinal length extending from the proximal end 30 to the distal end 32. The anchor 22 also has an outer surface 25 and an inner surface 26 that defines a lumen 28. In at least one embodiment, the anchor 22 is tubular. In some embodiments, the anchor 22 defines a valve region which is a part of the lumen 28 where a replacement valve is positioned during a transcatheter aortic valve implantation method which is discussed below in greater detail. In at least one embodiment, the anchor 22 is expandable. As used herein "expandable" refers to an increase in diameter from the delivery state and "diameter" is the distance of a straight line extending between two points and does not indicate a particular shape. The anchor 22 can be self-expanding, balloon expandable, or hybrid self-expanding and balloon expandable.

In some embodiments, the expansion member 24 is a balloon 24a, as shown for example in FIGS. 1-5C. In at least one embodiment, the balloon 24a has an outer wall 34 and an inner wall 36, and an interior lumen 50 defined by the outer wall 34 and the inner wall 36. In some embodiments, the interior lumen 50 is an inflation lumen. As can be seen from the figures, the balloon 24a is an annular balloon. The inner wall 36 defines a balloon lumen. In some embodiments, the balloon lumen has a diameter greater than a diameter of the anchor 22 so that the anchor 22 can be positioned within the balloon lumen. In at least one embodiment, as shown more clearly in FIG. 2, balloon 24a has two waist portions 72, 74 and a central portion 76 extending between the two waist portions 72, 74. As used herein, a "waist portion" is the portion of the balloon 24a where the outer wall 34 and the inner wall 36 are joined to one another. In one embodiment, the balloon 24a is a compliant balloon. In another embodiment, the balloon 24a is a semi-compliant balloon. In yet another embodiment, the balloon 24a is a non-compliant balloon. In at least one embodiment, the balloon 24a has a plurality of spines 38 positioned about the circumference of the inner wall 36 of the balloon 24a. In some embodiments, the spines 38 are formed on the interior surface of the inner wall 36 of the balloon 24a, as shown for example in FIG. 4. In at least one embodiment, the spines are coextruded with the inner wall 36 of the balloon 24a. In some embodiments, the spines 38 comprise a first material and at least the inner wall 36 of the balloon 24a is made of a second material, different then the first material. In one embodiment, the first material is stiffer than the second material. In at least one embodiment, the spines 38 extend longitudinally from the proximal waist portion 74 to the distal waist portion 72 of the balloon 24a.

In at least one embodiment, the balloon 24a is affixed at or substantially near the distal end 32 of the anchor 22. As used herein "affixed" indicates a permanent attachment. In some embodiments, the inner wall 36 of the balloon 24a is affixed to the anchor 22. In at least one embodiment, the balloon 24a is directly affixed to the outer surface 25 of the anchor 22 at the distal end 32 of the anchor (shown for example in FIG. 2). In at least one embodiment, the balloon 24a is only affixed to the anchor 22 at a distal end of the balloon 24a (shown for example in FIG. 2). Because the balloon 24a is only affixed to one end of the anchor 22, the proximal end 30 of the anchor 22 is free to move longitudinally relative to the distal end 32 of the anchor 22.

Figure 2:
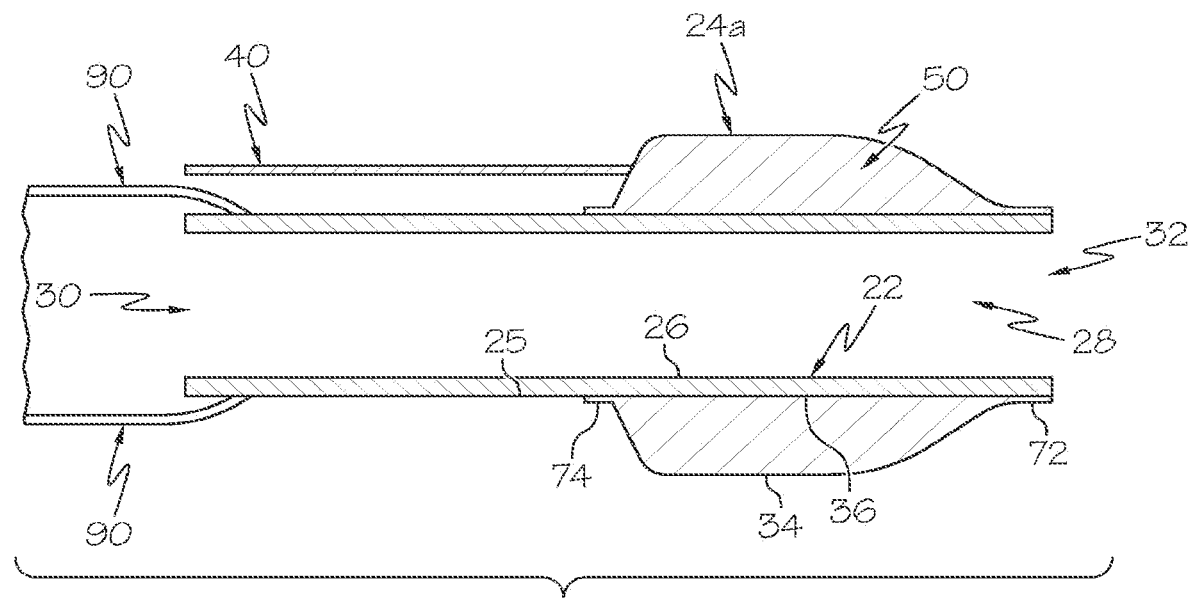
FIG. 2 is a cross-sectional view of the valvuloplasty device of FIG. 1 in the deployed configuration.

In some embodiments, such as shown in FIG. 2, only the distal waist portion 72 is directly affixed to the outer surface 25 of the anchor 22. The distal waist portion 72 is affixed to the outer surface 25 of the anchor 22 with adhesive, a suture, or other suitable attachment means. In at least one embodiment, the entire circumference of the distal waist portion 72 is affixed to the outer surface 25 of the anchor 22. In one embodiment, the distal waist portion 72 may also be directly affixed to a locking member attached to the anchor, such as those locking members described in U.S. Patent Publication Nos. 2005/0137686, 2005/0143809, and 2010/0280495, the entireties of each are incorporated by reference herein. As shown in FIG. 2, the proximal waist portion 74 is not directly affixed to the anchor 22. In at least one embodiment, both the distal waist portion 72 and the proximal waist portion 74 are affixed to the outer surface 25 of the anchor 22.

Figure 6A:
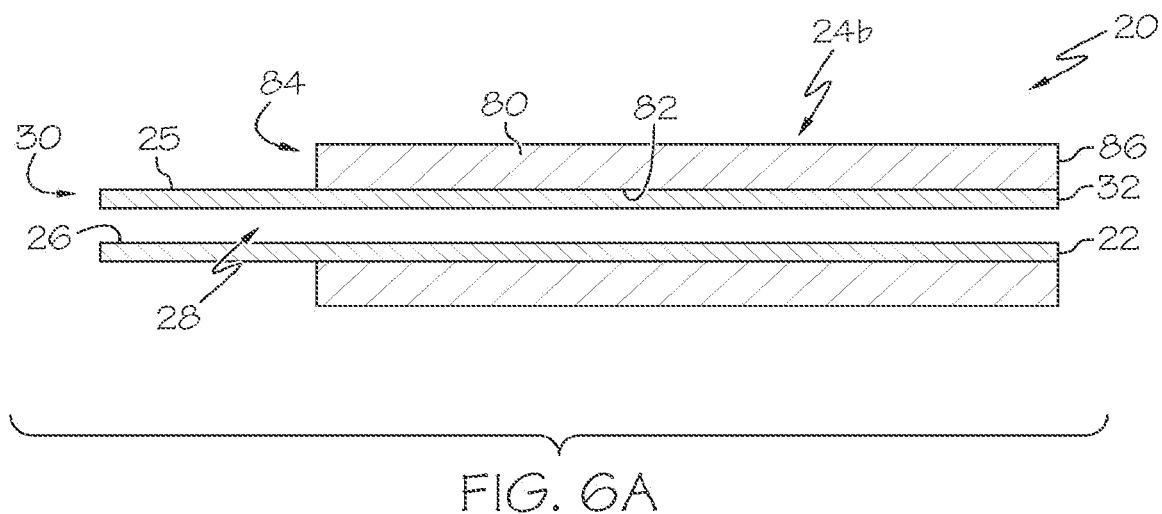
FIGS. 6A-6B are cross-sectional views of a valvuloplasty device in the delivery configuration and in the deployed configuration.
Figure 6B:
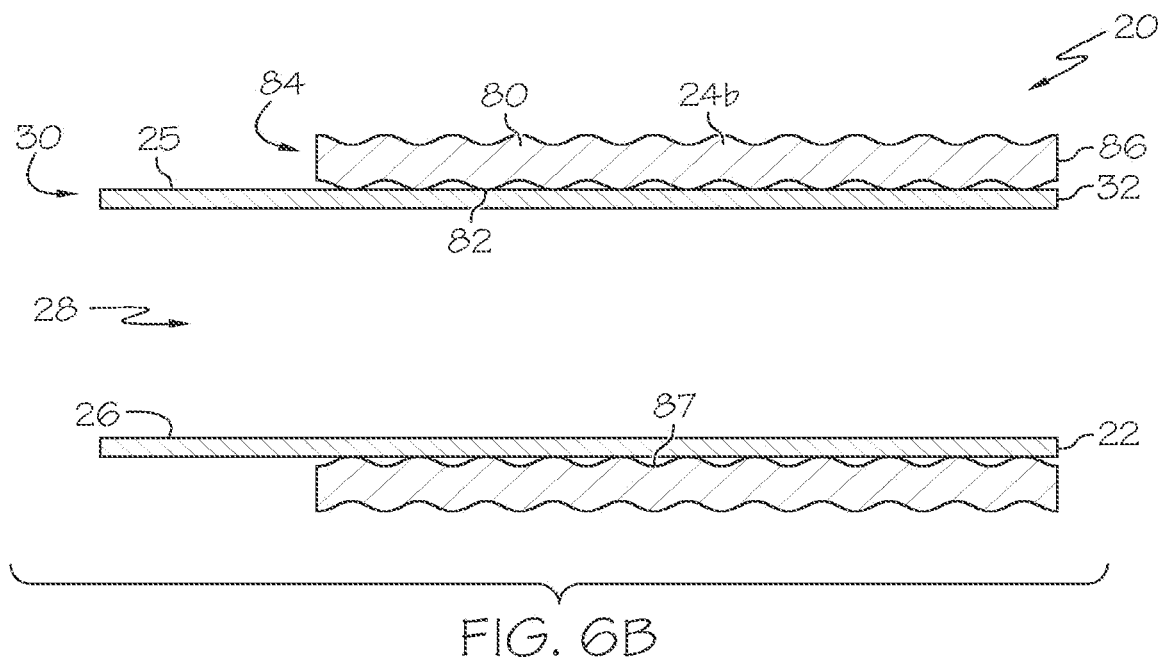

In other embodiments, the expansion member 24 is a sleeve 24b, as shown for example in FIGS. 6A-B. As shown in FIG. 6A, the sleeve 24b is tubular with a proximal end 84 and a distal end 86. In at least one embodiment, the sleeve 24b is affixed to the anchor 22 at at least one location. In some embodiments, both ends 84, 86 of the sleeve 24b are affixed to the anchor 22. In at least one embodiment, the sleeve 24b is affixed to the anchor 22 at a plurality of locations along the longitudinal length of the thick sleeve. In at least one embodiment the sleeve 24b has a greater thickness than the thickness of the anchor 22. In some embodiments, the sleeve 24b is at least twice as thick as the as the wall of the anchor 22. Thus, the sleeve 24b can be described as a thick sleeve.

In some embodiments, the sleeve 24b comprises compliant material, semi-compliant material, and combinations thereof Suitable means by which the sleeve 24b is affixed to the anchor 22 include sutures, adhesives such as glue, or molding, spraying, or dip coating the material for the thick sleeve onto the anchor so that the thick sleeve material encloses or wraps around the wires of the anchor 22.

As discussed below in greater detail, the anchor 22 has a delivery state and a deployed state; the expansion member 24 has a delivery state and a deployed state; and the valvuloplasty device has a delivery configuration, a partially deployed configuration, and a deployed configuration.

Figure 3:
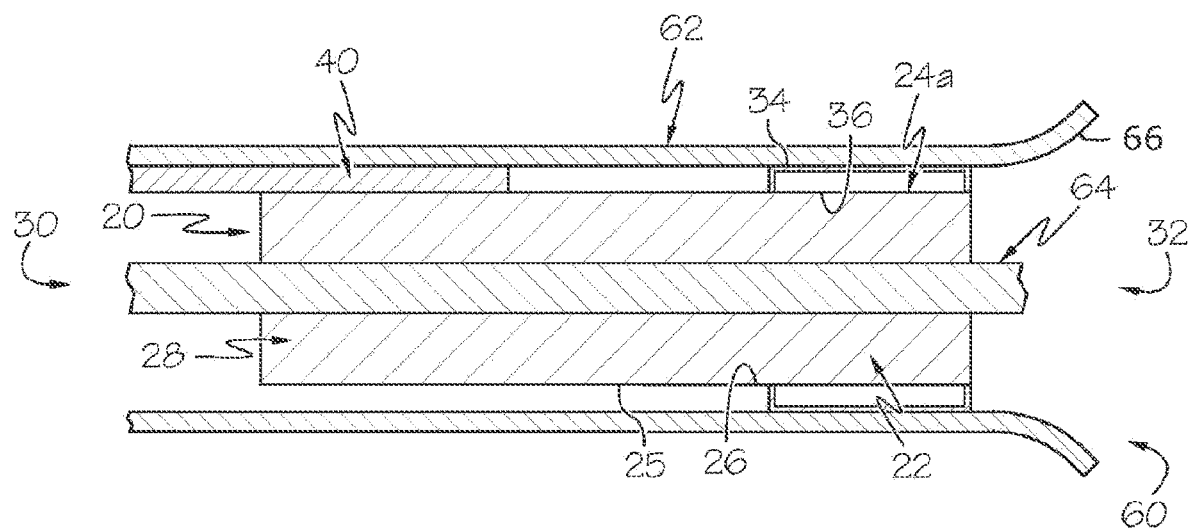
FIG. 3 is a cross-sectional view of the valvuloplasty device of FIG. 1 in a delivery configuration in a delivery device.
Figure 4:
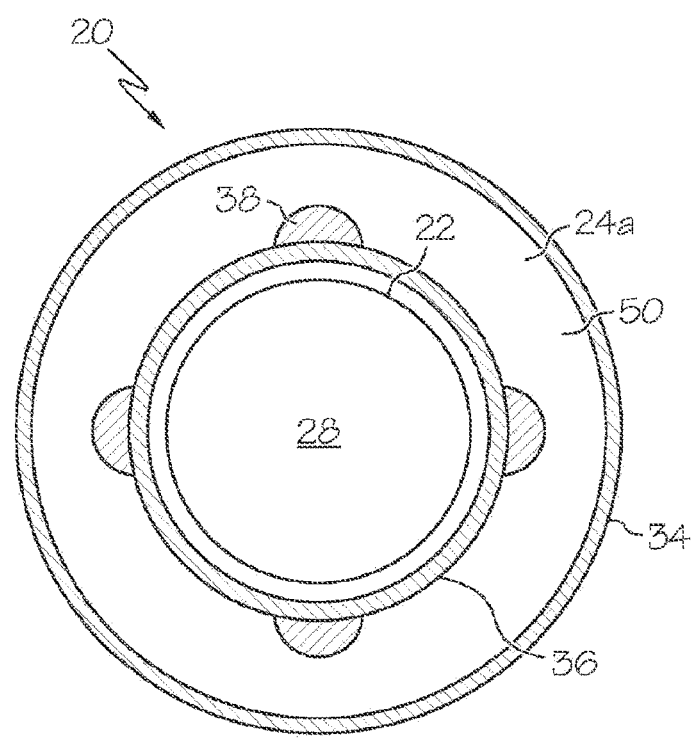
FIG. 4 is a cross-sectional view of the valvuloplasty device of FIG. 1.
Figure 5A:
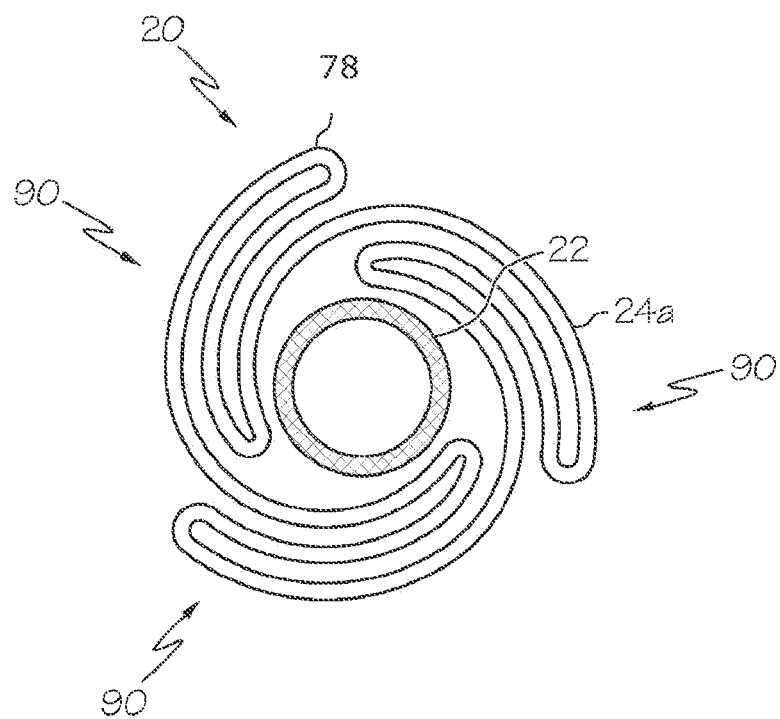
FIGS. 5A-5C are cross-sectional views of the valvuloplasty device of FIG. 1 in the delivery configuration, the partially deployed configuration, and the deployed configuration. For simplicity details regarding the thickness of the inner and outer walls of the balloon are omitted from FIGS. 5A-5B.
Figure 5B:
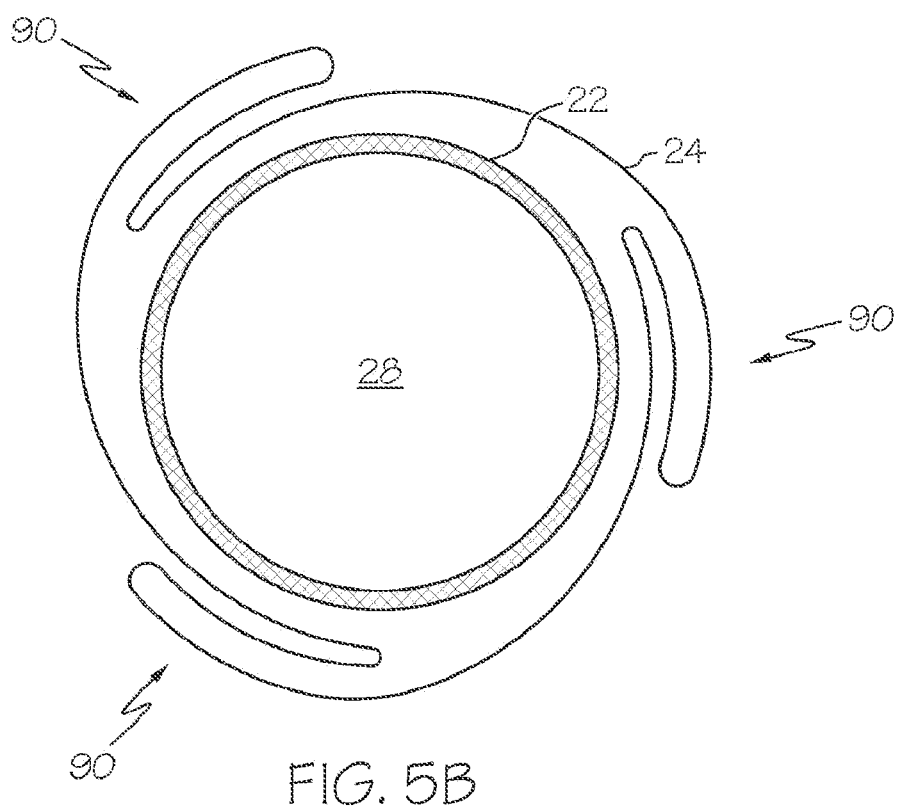
Figure 5C:
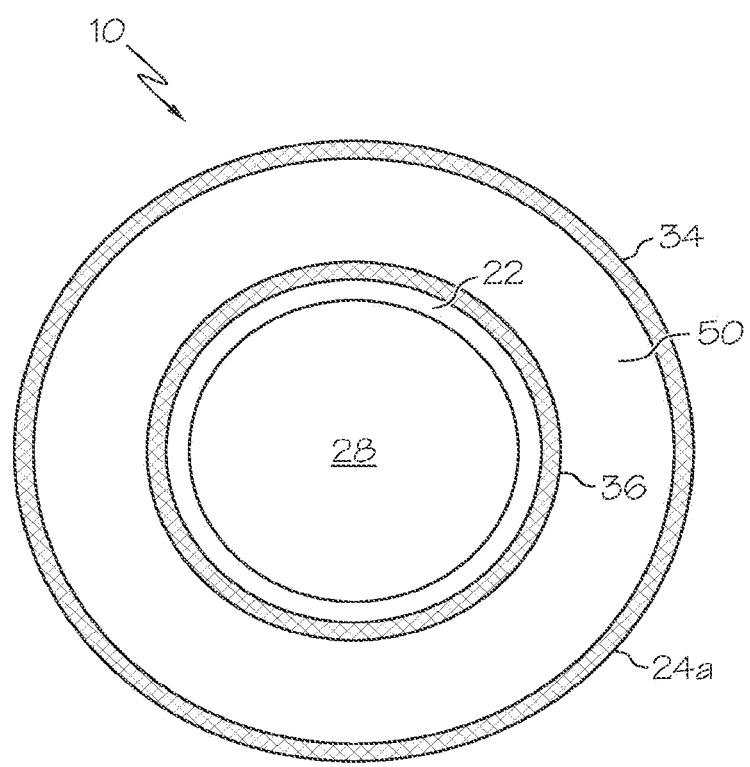

FIGS. 3, 5A, and 6A show the anchor 22 in the delivery state and FIGS. 2, 5B-C, and 6B show the anchor 22 in the deployed state. In at least one embodiment, the anchor 22 in the deployed state has a high radial force. In at least one embodiment, when the anchor 22 is in the delivery state, the anchor 22 has a first longitudinal length and a first diameter and when the anchor is in the deployed state, the anchor has a second longitudinal length and a second diameter. In some embodiments, the second diameter is greater than the first diameter. In other embodiments, the first longitudinal length is greater than the second longitudinal length. In these embodiments, the anchor can be described as being longitudinally compressed or foreshortened. In yet another embodiment, the second diameter is greater than the first diameter and the first longitudinal length is greater than the second longitudinal length. FIGS. 3 and 5A-B show the balloon 24a in the delivery state and FIGS. 2 and 5C show the balloon 24a in the deployed state. In at least one embodiment, the balloon 24a has a plurality of folds 78, as shown for example in FIGS. 5B-C. In some embodiments, both the outer wall 34 and the inner wall 36 form the folds. Thus, when the valvuloplasty device 20 is in the delivery configuration, there is some space between the unattached portions of the inner wall 36 of the balloon 24a and the outer surface 25 of the anchor 22. In at least one embodiment, the balloon 24a has three folds 78 when the balloon 24a is in the delivery state. In one embodiment, the diameter of the balloon 24a in the deployed state is greater than the diameter of the balloon 24a in the delivery state. In some embodiments, the balloon 24a is inflatable and is uninflated in the delivery state and inflated in the deployed state. In other embodiments, the balloon 24a comprises an electroactive polymer.

As shown in FIGS. 1-3, the balloon 24a extends axially over only a portion of the anchor 22 when the anchor 22 is in either the delivery state or the deployed state. In at least one embodiment, the balloon 24a extends longitudinally over at least a portion of the valve region of the anchor 22. In at least one embodiment, the balloon 24a and the anchor 22 are coterminous in one of the delivery state and the deployed state of the anchor 22. As used herein "coterminous" means that, with regard to two elements of the valvuloplasty device, the proximal ends of the two elements are radially aligned with one another and the distal ends of two elements are radially aligned with one another. Thus, two elements that are coterminus have the same longitudinal length. In this case, the balloon 24a and the anchor 22 have the same longitudinal length in one of the delivery state of the anchor 22 and the deployed state of the anchor 22.

In at least one embodiment, the balloon 24a in the deployed state has a constant cross-section in the central portion 76 (not shown). In some embodiments, the balloon 24a has a variable cross-section in the central portion 76, where the central portion 76 tapers towards the waist portions 72, 74, as shown for example in FIG. 2. In some embodiments, the taper to the proximal waist portion 74 is steeper, at an greater angle relative to the longitudinal axis of the valvuloplasty device 20, than the taper to the distal waist portion 72, as shown for example in FIG. 2.

FIGS. 3 and 5A show the valvuloplasty device 20 comprising an anchor 22 and a balloon 24a in the delivery configuration wherein both the anchor 22 and the balloon 24a are in the delivery state. FIG. 5B shows the valvuloplasty device in the partially deployed configuration wherein one of the anchor 22 or the balloon 24a is in the deployed state and the other is in the delivery state. FIGS. 2 and 5C show the valvuloplasty device in the expanded configuration wherein both the anchor 22 and the balloon 24a are in the deployed state. In at least one embodiment, as can be seen in FIGS. 5A-B, the balloon 24a has a plurality of folds 78 when the valvuloplasty device 20 is in the delivery configuration and when the valvuloplasty device 20 is in the partially deployed configuration.

In at least one embodiment, the valvuloplasty device 20 in a delivery configuration is carried by a delivery device 60. FIG. 3 shows an example of a delivery device 60. In at least one embodiment, the delivery device 60 has a tubular sheath 62.

In some embodiments, the delivery device 60 further comprises an inner member 64. In one embodiment, the inner member 64 is tubular and defines a guidewire lumen. In some embodiments, the inner member 64 may have an expansion balloon mounted thereon for expansion of the anchor 22. In at least one embodiment, the sheath 62 has a flared distal end 66, which can assist in retrieving the valvuloplasty device from the deployment location without the balloon 24a being pushed distally over itself.

In at least one embodiment, the anchor 22 self-expands by withdrawing the sheath 62 proximally to expose the anchor 22. In at least one embodiment, the anchor 22 is expanded by inflating the expansion balloon mounted on the inner member 64 has an expansion balloon mounted thereon. In at least one embodiment, the anchor 22 is longitudinally compressed by using an arrangement of locking mechanisms attached to the anchor 22, as discussed in U.S. Patent Publication Nos. 2005/0137686, 2005/0143809, and 2010/0280495, the entireties of each are incorporated by reference herein. In at least one embodiment, the anchor 22 is longitudinally compressed by using an arrangement of control wires or sutures attached to the distal end and tines attached to the proximal end. The tines act in the opposite direction to the control wires attached at the distal end, thereby foreshortening the anchor. In one embodiment, the tines can be a part of the anchor that is attached to the center of the inner member 64.

FIGS. 2 and 5C shows the valvuloplasty device 20 of FIG. 1 in a deployed configuration. In at least one embodiment, expansion of the balloon 24a occurs after expansion of the anchor 22. In some embodiments, the balloon 24a is inflatable and expanded by transmitting inflation media into the interior lumen 50 of the balloon 24a. In at least one embodiment, the inflation media is transmitted to the balloon 24a by a detachable inflation mechanism 40, which is in fluid communication with a fluid source and the interior lumen 50 of the balloon 24a. In some embodiments, the detachable inflation mechanism is detachably connected to a valve in the balloon's outer wall (not shown). When the inflation mechanism is detached from the balloon, the valve prevents fluid from escaping the inflation lumen. In some embodiments, the detachable inflation mechanism 40 extends from a proximal end of the balloon 24a along the outer surface of the anchor 22 to a proximal end of a delivery device 60. In other embodiments, the detachable inflation mechanism extends from a distal end of the balloon through the distal end of the anchor and through the lumen of the anchor to a proximal end of a delivery device 60 (not shown).

In at least one embodiment, a valvuloplasty device 20 comprising an anchor 22 and a sleeve 24b has a delivery configuration wherein both the anchor 22 and the sleeve 24b are in the delivery state, as shown for example in FIG. 6A and a deployed configuration wherein both the anchor 22 and the sleeve 24b are in the deployed state, as shown for example in FIG. 6B. As can be seen in FIG. 6A, the sleeve 24b has a smooth outer surface 80 and a smooth inner surface 82 when the sleeve 24b is in the delivery state. As can be seen in FIG. 6B, when the sleeve 24b is in the deployed state both the outer surface 80 and the inner surface 82 have large corrugations with a plurality of troughs and peaks. In at least one embodiment, the sleeve 24b extends axially over only a portion of the anchor 22 when the anchor 22 is in either the delivery state or the deployed state. In at least one embodiment, the sleeve 24b and the anchor 22 are coterminous in one of the delivery state and the deployed state of the anchor (not shown). In at least one embodiment, the sleeve 24b is in the delivery state when the anchor 22 is in the delivery state and the sleeve 24b is in the deployed state when the anchor 22 is in the deployed state. In some embodiments, the sleeve 24b has a first longitudinal length when the valvuloplasty device 20 is in the delivery configuration and a second longitudinal length less than the first longitudinal length when the valvuloplasty device 20 is in the deployed configuration.

In at least one embodiment, when the anchor 22 is foreshortened or longitudinally compressed to the deployed state, as discussed above, the sleeve 24b foreshortens and has a plurality of peaks and troughs that form large ripples, waves, or corrugations, as shown in FIG. 6B. For simplicity, corrugations will be used hereinafter. In some embodiments, there are gaps 87 between the inner surface 82 of the sleeve 24b and the outer surface of the anchor 22 when the sleeve 24b is in the expanded state. As can be seen, the gaps 87 are between the inner surface of a peak and the outer surface of the anchor 22. In at least one embodiment, the corrugations extend from the proximal end 84 to the distal end 86 of the sleeve 24b.

In some embodiments, the troughs of the plurality of corrugations are the portions of the sleeve 24b that are affixed to the anchor 22 and the peaks of the plurality of corrugations are the portions of the sleeve 24b that are unaffixed to the anchor 22. In other words, the attachment locations of the sleeve 24b to the anchor 22 form the troughs of the plurality of corrugations. In at least one embodiment, the sleeve 24b extends a maximum distance from the outer surface 25 of the anchor 22 that is greater when the sleeve 24b is in the expanded state than when the sleeve 24b is in the delivery state. In at least one embodiment, a sleeve with corrugations mimics a balloon. In at least one embodiment, the delivery device 60 includes a control mechanism 90 releasably engaged to the valvuloplasty device 20. In some embodiments, the control mechanism 90 is engaged to the anchor 22, as shown for example in FIG. 2. In some embodiments, the control mechanism 90 allows an operator to retrieve the valvuloplasty device 20 from the bodily lumen or to change the position of the valvuloplasty device 20 within the bodily lumen. Thus, the mechanism 90 can also be considered a retrieval mechanism. The retrieval mechanism 90 in one embodiment comprises at least one suture line or wire woven through an opening extending between the outer surface 25 and the inner surface 26 of the anchor 22. In some embodiments, proximally withdrawing the control mechanism 90 longitudinally lengthens the anchor. Thus, the control mechanism 90 can be used to move the valvuloplasty device 20 from the deployed configuration to the delivery configuration.

In at least one embodiment, when the valvuloplasty device 20 is in the deployed configuration at the deployment location, the radial forces caused the balloon 24a, or sleeve 24b, in the deployed state assist in expanding the patient's native valve, such as by opening the valve leaflets wider and cracking mineral deposits to make the valve leaflets more flexible. Additionally, in at least one embodiment, the lumen 28, of the anchor 22 acts as a single perfusion channel for blood to pass through the valvuloplasty device 20. In at least one embodiment, the lumen 28 is much larger than the channels of the perfusion balloons that are typically used in balloon aortic valvuloplasty. For example, in at least one embodiment, the lumen 28 of the anchor 22 has an effective orifice area greater than 1 mm.sup.2 In some embodiments, the large single perfusion channel greatly reduces the pressure gradient between the ventricle and the aorta during valvuloplasty relative to the pressure gradient of prior art balloon aortic valvuloplasty. In some embodiments, this reduced pressure gradient prevents movement of the balloon and/or allows deployment of the valvuloplasty device 20 without the use of pacing.

In at least one embodiment, the valvuloplasty device 20 is used for valvuloplasty where the valvuloplasty device 20 is used to increase the valve area prior to the subsequent deployment of a replacement valve. In some embodiments, the valvuloplasty method is a balloon aortic valvuloplasty method. Suitable inflation media to inflate the balloon for a valvuloplasty method includes media that can be removed from the annular balloon in order to deflate the balloon.

In at least one embodiment, the valvuloplasty device 20 is used for valve implantation. In some embodiments, the valve implantation method is a transcatheter aortic valve implantation method. Thus, in some embodiments, the valvuloplasty device 20 is used as part of a system including a replacement heart valve. In some embodiments, the balloon 24a is compliant so that when inflated, the balloon 24a fills out gaps between the native valve and the aortic wall to prevent paravalvular leaks. In other embodiments, the sleeve 24b in the deployed state fills out gaps between the native valve and the aortic wall to prevent paravalvular leaks.

Using the valvuloplasty devices 20 described herein, a valvuloplasty method such as BAV, and an implantation method such as TAVI, each include at least some of the following steps:

1) advancing the valvuloplasty device 20 to a desired deployment location in the vascular system;
  i) wherein the desired deployment location is a native heart valve;
  ii) wherein the valvuloplasty device 20 comprises an anchor 22 and a balloon 24a;
  iii) wherein the valvuloplasty device 20 comprises an anchor 22 and a sleeve 24b;
2) expanding the anchor 22 from a delivery state to a deployed state;
  i) wherein the sheath of the delivery device is withdrawn and the anchor self expands;
  ii) wherein a balloon of the delivery device expands the anchor;
  iii) wherein the longitudinal length of the anchor decreases during expansion;
  iv) wherein the sleeve 24b foreshortens and has a plurality of corrugations when the anchor is expanded;
3) expanding the balloon 24a from a delivery state to a deployed state;
  i) wherein the balloon is expanded after the anchor is in the deployed state;
  ii) wherein the balloon is inflatable and is expanded by the introduction of inflation media into the interior lumen.

The valvuloplasty method further includes at least some of the following steps:

4) removing the valvuloplasty device 20 from the vascular system;
  wherein the step of removing may include one or more of the following steps:
  i) deflating the balloon 24a by removing the inflation media from the interior lumen 50 through the inflation mechanism 40;
  ii) lengthening the anchor;
    a) wherein the anchor is lengthened by a control mechanism comprising at least one suture line or wire woven through an opening extending between the outer surface 25 and the inner surface 26 of the anchor 22;
  ii) resheathing the valvuloplasty device 20 with the sheath 62 of the delivery device 60, and removing the delivery device 60 with the valvuloplasty device 20 positioned within;
    a) wherein the sheath 62 has a flared distal end.

The implantation method further includes at least some of the following steps:

4) removing the detachable inflation mechanism 40 from the valvuloplasty device 20; and
5) placing a replacement valve within lumen 28 of the anchor 22 (not shown);
6) expanding the replacement valve.

Suitable inflation media to inflate the balloon 24a for the implantation method include hardenable and non-hardenable media since the balloon 24a in this method is implanted in the bodily lumen and thus does not need to be deflated.

In some embodiments of the implantation methods discussed above, a single delivery device deploys valvuloplasty device 20 and the replacement valve. In other embodiments of the implantation methods discussed above, one delivery device deploys the valvuloplasty device and another delivery device deploys the replacement valve. In at least one embodiment, the valvuloplasty device is expanded from the delivery configuration to the deployed configuration before the replacement valve is positioned within the lumen 28 of the anchor 22.

In some embodiments, the replacement valve for the implantation methods such as TAVI, disclosed herein includes leaflets that may comprise bovine tissue, synthetic tissue, silicone, polymer or other materials having suitable and/or similar properties of the leaflets of a native valve. Features of the replacement valve that may be incorporated into this and other embodiments can be found at least in U.S. Pat. Nos. 7,329,279, 7,381,219, 7,445,631, 7,748,389, 7,780,725, 7,824,442, 7,824,443; U.S. Patent Publication Nos. 2005/0112355, 2005/0137686, 2005/0137687, 2005/0137688, 2005/0137689, 2005/0137691, 2005/0137692, 2005/0137694, 2005/0137695, 2005/0137696, 2005/0137697, 2005/0137701, 2005/0143809, 2006/0058872, 2006/0173524, 2006/0253191, 2007/0010876, 2007/0024452, 2007/0112355, 2007/0118214, 2007/0162107, 2007/0203503, 2008/0125859, 2008/0234814, 2009/0076598, 2009/0054969, 2009/0264997, 2010/0121434, 2010/0280495; and WO Publication Nos. 2005/062980, 2005/065585, 2006/009690, 2007/053243, 2007/058847, each which are incorporated by reference herein in their entireties.

In some embodiments, the anchor 22 is a stent, a graft, or a stent-graft. As discussed above, the anchor 22 may be created by methods including cutting or etching a design from a tubular stock, from a flat sheet which is cut or etched and which is subsequently rolled, or from one or more interwoven wires or braids. Any other suitable technique which is known in the art or which is subsequently developed may also be used to manufacture the anchor 22 disclosed herein. In at least one embodiment, the anchor 22 is a braided stent. In some embodiments, the anchor 22 has a plurality of openings extending from the outer surface 25 to the inner surface 26.

The anchor 22 may be made from any suitable non-biodegradabale biocompatible material(s) including one or more polymers, one or more metals or combinations of polymer(s) and metal(s). Polymers that may be used include polyester, polyamide, polyoxymethylene, polyurethane, silicone, polycarbonate, various copolymers such as but not limited to polyetherester, polyetheramide, and combinations thereof. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The anchor 22 may be made of shape memory materials, such as Nitinol, or may be made of materials which are plastically deformable. In the case of shape memory alloys, the shape memory alloy forming the anchor 22 may be provided with shape memory effect properties or superelastic properties, as is known in the art. An anchor 22 made of a shape memory alloy with shape memory effect properties restores itself to its memorized shape upon being heated to a transition temperature and having any restraints removed therefrom. An anchor 22 made of a shape memory alloy with superelastic properties reverts to a prior configuration upon removal of a load. Non-limiting examples of compliant material include, but are not limited to, nylon and polyamines.

Non-limiting examples of non-compliant materials include, but are not limited to, polyethylene terephthalates, polyacrylenesulfide, and copolyesters.

Non-limiting examples of semi-compliant materials include, but are not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. Other suitable materials may also be used for the balloon 24a and the sleeve 24b.

Other suitable materials for the sleeve 24b include, but are not limited to, Poly(Styrene-Isobutylene-Styrene) Tri-block polymer (SIBS), polyurethane, an elastic polymer, woven fabric, a multi-walled membrane of polymer, and combinations thereof In some embodiments the valvuloplasty device 20, the delivery device 60, or other portion of the assembly may include one or more areas, bands, coatings, members, etc. that is (are) detectable by imaging modalities such as X-Ray, MRI, ultrasound, etc. In some embodiments at least a portion of the valvuloplasty device 20 is at least partially radiopaque. For example, in at least one embodiment, the valvuloplasty device 20 includes at least one area, band, coating, or member that is detectable by imaging modalities.

In some embodiments the at least a portion of the valvuloplasty device 20 is configured to include one or more mechanisms for the delivery of a therapeutic agent. Often the agent will be in the form of a coating or other layer (or layers) of material placed on a surface region of the valve, which is adapted to be released at the site of the valve's implantation or areas adjacent thereto.

The following numbered statements describe the valvuloplasty device discussed above.

1. A valvuloplasty device comprising:
an expandable anchor having a proximal end, a distal end, an outer surface extending between the proximal end and the distal end, and an inner surface extending between the proximal end and the distal end, the inner surface defining a lumen; and an expansion member selected from the group consisting of:
an annular expandable balloon having an inner surface and an outer surface, the annular balloon disposed about the outer surface of the expandable anchor such that the inner surface of the balloon directly contacts the outer surface of the expandable anchor; and
a sleeve disposed about the outer surface of the expandable anchor.

2. The valvuloplasty device of statement 1, wherein the anchor is a stent.

3. The valvuloplasty device of statement 2, wherein the stent is a braided stent.

4. The valvuloplasty device of statements 1-3, wherein the anchor is self-expandable.

5. The valvuloplasty device of statements 1-4 wherein the anchor comprises a shape memory alloy with superelasticity.

6. The valvuloplasty device of statements 1-5, wherein the expansion member is affixed to at least one location on the outer surface of the expandable anchor.

7. The valvuloplasty device of statements 1-6, wherein the distal end of expansion member is affixed to the distal end of the anchor.

8. The valvuloplasty device of statements 1-7, wherein the proximal end of the expansion member is unaffixed to the anchor.

9. The valvuloplasty device of statements 1-8, wherein the expansion member extends axially over at least a portion of the expandable anchor.

10. The valvuloplasty device of statements 1-9, wherein the valvuloplasty device has:
a delivery configuration wherein the expandable anchor is in a delivery state and the expansion member is in a delivery state;
a deployed configuration, wherein the expandable anchor is in an deployed state and the expansion member is in the deployed state.

11. The valvuloplasty device of statements 1-10, wherein the expansion member is the sleeve, the sleeve in the delivery state having a smooth outer surface and a smooth inner surface, and the sleeve in the deployed state having a corrugated outer surface and a corrugated inner surface.

12. The valvuloplasty device of statements 1-7 and 9-11, wherein the sleeve has a plurality of attachment locations where the sleeve is affixed to the anchor, wherein when the sleeve is in the deployed state the plurality of attachments locations form troughs of the plurality of corrugations.

13. The valvuloplasty device of statements 1-7 and 9-12, the sleeve having a first thickness, the anchor having a second thickness less than the first thickness.

14. The valvuloplasty device of statements 1-10, wherein the expansion member is the balloon, the balloon being inflatable, the balloon in the delivery state being uninflated, the balloon in the deployed state being inflated.

15. The valvuloplasty device of statements 1-10 and 14, the balloon being either a compliant balloon, a semi-compliant balloon, or a non-compliant balloon.

16. The valvuloplasty device of statements 1-10 and 14-15, the balloon further comprising:
    an outer wall forming the outer surface of the balloon;
    an inner wall forming the inner surface of the balloon;
    a proximal waist portion; and
    a distal waist portion;
    wherein the outer wall and the inner wall are affixed to one another to form the proximal waist portion and the distal waist portion, the outer and inner walls defining a balloon inflation lumen.

17. The valvuloplasty device of statements 1-10 and 14-16, wherein only the distal waist portion of the balloon is affixed to the anchor.

18. The valvuloplasty device of statements 1-10 and 14-17, the balloon further comprising a plurality of spines positioned about the circumference of the inner wall of the balloon.

19. The valvuloplasty device of statement 18, the plurality of spines being made of a first material, the inner wall being made of a second material different than the first material.

20. The valvuloplasty device of statement 19, the first material being stiffer than the second material.

21. The valvuloplasty device of statements 18-20, each spine extending from the proximal waist portion to the distal waist portion of the balloon.

22. The valvuloplasty device of statements 1-10 and 14-21, the valvuloplasty device further having a partially deployed configuration wherein the expandable anchor is in the deployed state and the balloon is in the delivery state.

23. The valvuloplasty device of statements 1-10 and 14-22, wherein the balloon has a plurality of folds when the expandable anchor is in the delivery state.

24. The valvuloplasty device of statements 1-23, wherein the anchor lumen has an effective orifice area greater than 1 mm.sup.2 when the anchor is in the deployed state.

25. The valvuloplasty device of statements 1-24, wherein when deployed at the site of a native heart valve, the anchor lumen reduces the pressure gradient between the ventricle and aorta which provides for the deployment of the valvuloplasty device without pacing.

26. The valvuloplasty device of statements 1-25, wherein the anchor has a first longitudinal length in the delivery state and a second longitudinal length in the deployed state, wherein the second longitudinal length is greater than the first longitudinal length.

27. The valvuloplasty device of statements 1-26 further comprising a replacement valve positioned within the lumen of the anchor.

28. The valvuloplasty device of statements 1-27 in combination with a delivery device, the delivery device comprising an outer sheath, the outer sheath defining a sheath lumen, the valvuloplasty device positioned within the sheath lumen.

29. The valvuloplasty device of statement 28, wherein the outer sheath has a flared distal end.

30. The valvuloplasty device of statements 28-29, the delivery device further comprising an inner member, the inner member positioned within the lumen of the anchor.

31. The valvuloplasty device of statements 28-30, further comprising an inflation mechanism detachably connected to the balloon of the valvuloplasty device.

32. The valvuloplasty device of statement 31, the inflation mechanism defining an inflation lumen in fluid communication with a balloon inflation lumen and with a fluid source.

33. The valvuloplasty device of statements 31-32, the balloon further comprising a valve, the inflation mechanism detachably connected to the valve.

34. The valvuloplasty device of statements 28-33, further comprising a control mechanism, the control mechanism releasably engaged to the valvuloplasty device.

35. The valvuloplasty device of statement 34, the control mechanism comprising at least one suture line or wire.

36. The valvuloplasty device of statement 35, wherein the at least one suture line or wire is woven through an opening extending between the outer surface and the inner surface of the anchor.

37. The valvuloplasty device of statements 34-36, wherein the control mechanism is configured to longitudinally lengthen the anchor.

38. The valvuloplasty device of statements 1-37 used for a valvuloplasty method or a valve implantation method.

39. The valvuloplasty device of statement 38, wherein the valvuloplasty and the valve implantation method each include the following steps:
    advancing the delivery device with the valvuloplasty device to a desired deployment location in the vascular system; and
    deploying the anchor of the valvuloplasty device.

40. The valvuloplasty device of statement 39, wherein deploying the anchor includes withdrawing the sheath of the delivery device.

41. The valvuloplasty device of statements 39-40, wherein the longitudinal length of the anchor decreases during deploying.

42. The valvuloplasty device of statements 39-41, wherein the valvuloplasty device comprises the sleeve, wherein when the anchor is in the deployed state, the sleeve is in the deployed state and has a plurality of corrugations.

43. The valvuloplasty device of statements 39-41, wherein the valvuloplasty device comprises the balloon, wherein the balloon aortic valvuloplasty and the transcatheter aortic valve implantation method further includes expanding the balloon from the delivery state to the deployed state.

44. The valvuloplasty device of statement 43, wherein the balloon is expanded after the anchor is deployed.

45. The valvuloplasty device of statements 43-44, wherein the balloon is inflatable and is expanded by inflation media by a detachable inflation mechanism.

46. The valvuloplasty device of statements 39-45, wherein the valvuloplasty method further comprises:
    removing the valvuloplasty device from the deployment location.

47. The valvuloplasty device of statement 46, wherein removing the valvuloplasty device comprises deflating the balloon.

48. The valvuloplasty device of statements 46-47 wherein removing the valvuloplasty device comprises lengthening the anchor.

49. The valvuloplasty device of statements 48, wherein the anchor is lengthened by a control mechanism.

50. The valvuloplasty device of statements 46-49, wherein removing the valvuloplasty device comprises withdrawing the valvuloplasty device within the outer sheath of the delivery device.

51. The valvuloplasty device of statements 39-50, wherein the outer sheath of the delivery device has a flared distal end.

52. The valvuloplasty device of statements 39-45, wherein the transcatheter aortic valve implantation method further comprises:
removing the detachable inflation mechanism from the balloon.

53. The valvuloplasty device of statement 52, further comprising placing a replacement valve within the lumen of the anchor The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from originally filed claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. originally filed claim 3 may be taken as alternatively dependent from originally filed claim 1; originally filed claim 4 may be taken as alternatively dependent on originally filed claim 1, or on originally filed claim 3; originally filed claim 6 may be taken as alternatively dependent from originally filed claim 5; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of performing valvuloplasty, comprising:
advancing a valvuloplasty device to a deployment location within a vascular system;
wherein the valvuloplasty device comprises:
an expandable anchor having a proximal end, a distal end, an outer surface extending between the proximal end and the distal end, and an inner surface extending between the proximal end and the distal end, the inner surface defining a lumen; and
an expansion member comprising:
an annular expandable balloon having an inner surface and an outer surface, the annular expandable balloon disposed around the outer surface of the expandable anchor such that at least a portion of the inner surface of the annular expandable balloon is affixed directly to the outer surface of the expandable anchor;
deploying the expandable anchor from a delivery state to a deployed state, thereby permitting fluid flow through the lumen of the expandable anchor;
expanding the expansion member; and
removing the valvuloplasty device from the vascular system.

2. The method of claim 1, wherein the expansion member extends axially over at least a portion of the expandable anchor.

3. The method of claim 2, wherein the distal end of the expandable anchor is radially aligned with a distal end of the expansion member.

4. The method of claim 1, wherein the valvuloplasty device has:
a delivery configuration wherein the expandable anchor is in the delivery state and the expansion member is in a delivery state;
a deployed configuration, wherein the expandable anchor is in the deployed state and the expansion member is in a deployed state.

5. The method of claim 4, the annular expandable balloon being inflatable, the annular expandable balloon in the delivery state being uninflated, the annular expandable balloon in the deployed state being inflated.

6. The method of claim 5, the valvuloplasty device further having a partially deployed configuration wherein the anchor is in the deployed state and the annular expandable balloon is in the delivery state.

7. The method of claim 5, wherein the annular expandable balloon has a plurality of folds when the expandable anchor is in the delivery state.

8. The method of claim 5, wherein the annular expandable balloon has a plurality of spines engaged to an inner wall of the annular expandable balloon, the plurality of spines being positioned about a circumference of the inner wall of the annular expandable balloon.

9. The method of claim 1, further comprising deploying a replacement valve implant within the lumen of the expandable anchor.

10. A method of performing valvuloplasty, comprising:
advancing a valvuloplasty device to a deployment location within a vascular system;
wherein the valvuloplasty device comprises:
an expandable anchor having a proximal end, a distal end, an outer surface extending between the proximal end and the distal end, and an inner surface extending between the proximal end and the distal end, the inner surface defining a lumen having open ends; and
an annular expandable balloon having an inner surface and an outer surface, the annular expandable balloon disposed around the outer surface of the expandable anchor such that at least a portion of the inner surface of the annular expandable balloon is affixed directly to the outer surface of the expandable anchor;

deploying the expandable anchor from a delivery state to a deployed state, thereby permitting fluid flow through the lumen of the expandable anchor;

thereafter, inflating the expandable annular balloon; and removing the valvuloplasty device from the vascular system.

11. The method of claim 10, wherein the expandable anchor is self-expanding, and deploying the expandable anchor includes withdrawing a delivery sheath relative to the expandable anchor to expose the expandable anchor at the deployment location.

12. The method of claim 10, wherein the valvuloplasty device includes an expansion balloon mounted on an inner member disposed within the lumen of the expandable anchor, and deploying the expandable anchor includes inflating the expansion balloon within the lumen of the expandable anchor.

13. The method of claim 10, wherein after deploying the expandable anchor to the deployed state, the expandable anchor engages a wall of the vascular system at the deployment location.

14. The method of claim 13, wherein in the deployed state the lumen of the expandable anchor has an effective orifice area greater than 1 square millimeter.

15. The method of claim 10, wherein the valvuloplasty device includes an inflation mechanism detachably connected to the expandable annular balloon.

16. The method of claim 10, wherein inflating the expandable annular balloon includes expanding the expandable annular balloon from a delivery state to a deployed state, the outer surface of the expandable annular balloon engaging a wall of the vascular system at the deployment location preventing fluid flow between the wall of the vascular system and the outer surface of the expandable anchor.

17. The method of claim 10, further comprising deploying a replacement valve implant within the lumen of the expandable anchor.

18. The method of claim 10, wherein at least a portion of the inner surface of the annular expandable balloon is affixed directly to the outer surface of the expandable anchor at the distal end of the expandable anchor.

19. The method of claim 10, wherein the expandable annular balloon is only affixed to the expandable anchor at a distal end of the expandable annular balloon.

* * * * *